(12) United States Patent
Hendriks et al.

(10) Patent No.: US 9,861,427 B2
(45) Date of Patent: Jan. 9, 2018

(54) ELECTRO-SURGICAL SYSTEM, AN ELECTRO-SURGICAL DEVICE, AND A METHOD FOR OPERATING AN ELECTRO-SURGICAL SYSTEM

(71) Applicant: KONINKLIJKE PHILIPS N.V., Eindhoven (NL)

(72) Inventors: Bernardus Hendrikus Wilhelmus Hendriks, Eindhoven (NL); Theodoor Jacques Marie Ruers, Eindhoven (NL); Gerhardus Wilhelmus Lucassen, Eindhoven (NL); Manfred Mueller, Eindhoven (NL); Jeroen Jan Horikx, Weert (NL); Waltherus Cornelis Jozef Bierhoff, Veldhoven (NL); Jasper Klewer, Utrecht (NL); Marjolein Van Der Voort, Valkenswaard (NL); Neriman Nicoletta Kahya, Eindhoven (NL); Christian Reich, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 842 days.

(21) Appl. No.: 14/372,777

(22) PCT Filed: Jan. 16, 2013

(86) PCT No.: PCT/IB2013/050402
§ 371 (c)(1),
(2) Date: Jul. 17, 2014

(87) PCT Pub. No.: WO2013/108194
PCT Pub. Date: Jul. 25, 2013

(65) Prior Publication Data
US 2015/0005765 A1    Jan. 1, 2015

Related U.S. Application Data

(60) Provisional application No. 61/588,748, filed on Jan. 20, 2012.

(51) Int. Cl.
*A61B 18/14* (2006.01)
*A61B 18/12* (2006.01)
(Continued)

(52) U.S. Cl.
CPC ...... *A61B 18/1402* (2013.01); *A61B 18/1233* (2013.01); *A61B 2017/00057* (2013.01);
(Continued)

(58) Field of Classification Search
CPC .......... A61B 18/14202; A61B 18/1233; A61B 2017/00057; A61B 2017/0061
See application file for complete search history.

(56) References Cited

U.S. PATENT DOCUMENTS 4,273,127 A   6/1981 Auth et al.
5,762,609 A   6/1998 Benaron et al.
(Continued)

FOREIGN PATENT DOCUMENTS

CN   201179110 Y   1/2009
DE   10249674      5/2004
(Continued)

OTHER PUBLICATIONS

T.J. Farrell, et al., "A Diffusion Theory Model of Spatially Resolved, Steady-State Diffuse Reeflectance for the Noninvasive Determination of Tissue Optical Properties in Vivo", Med. Phys., 19(4), Jul./Aug. 1992, pp. 879-888.
(Continued)

*Primary Examiner* — Joseph Dietrich

(57) ABSTRACT

An electro-surgical system (100) with an optical feedback functionality for performing electro-surgery on tissue (200)
(Continued)

of patient. An electro-surgical device (105) has an electrode portion (110) with an optical guide (114) integrated therein. An optical unit (160) performs optical characterization of tissue type and/or condition, and is arranged for performing an analysis of the tissue type and/or condition. A control unit (170) generates a feedback control signal (FEEDCON) based on the analysis of the tissue type and/or condition, optical guide allows inspecting the tissue that is e.g. just a few millimeters ahead of the electrode portion (110) performing e.g. the cutting. As a result of the fast and reliable analysis performed by the spectrometer in the optical unit according to the present invention, the system can proactively react to what kind of tissue is in front of the electro-surgical portion i.e. the 'blade' of the electro-surgical device or the electro-surgical 'knife'.

12 Claims, 9 Drawing Sheets

(51) Int. Cl.
*A61B 17/00* (2006.01)
*A61B 18/00* (2006.01)

(52) U.S. Cl.
CPC ............... *A61B 2017/00061* (2013.01); *A61B 2018/0091* (2013.01); *A61B 2018/00642* (2013.01); *A61B 2018/00648* (2013.01)

(56) References Cited

U.S. PATENT DOCUMENTS

| | | |
|---|---|---|
| 5,769,791 A | 6/1998 | Benaron et al. |
| 5,843,000 A | 12/1998 | Nishioka et al. |
| 7,749,217 B2 | 7/2010 | Podhajsky |
| 2006/0100614 A1 | 5/2006 | Long |
| 2006/0173359 A1 | 8/2006 | Lin et al. |
| 2009/0088772 A1 | 4/2009 | Blumenkranz |
| 2015/0005765 A1 | 1/2015 | Hendriks et al. |

FOREIGN PATENT DOCUMENTS

| | | |
|---|---|---|
| GB | 2414679 | 7/2006 |
| WO | WO0174252 | 10/2001 |
| WO | WO02083003 | 10/2002 |
| WO | WO2008011056 | 1/2008 |
| WO | WO2009090588 | 7/2009 |
| WO | WO2011104664 | 9/2011 |
| WO | WO2012049621 | 4/2012 |

OTHER PUBLICATIONS

R. Nachabe, et al., "Effect of Bile Absorption Coefficients on the Estimation of Liver Tissue Optical Properties and Related Implications in Discriminating Healthy and Tumourous Samples", Biomedical Optics Express, vol. 2, No. 3, Mar. 1, 2011, pp. 600-614.
R. Nachabe, et al., "Estimation of Biological Chromophores Using Diffuse Optical Spectroscopy: Benefit of Extending the UV-VIS Wavelength Range to Include 100 to 16 NM", Optics Express, vol. 18, No. 24, Nov. 22, 2010, pp. 1432-1442.
R. Nachabe, et al., "Estimation of Lipid Water Concentrations in Scattering media with Diffuse Optical Spectroscopy from 900 to 1600 NM", Journal of Biomedical Optics, vol. 15(3), May/Jun. 2010, pp. 1-1 through 1-10.
Q. Zhang, et al., "Turbidity-Free Fluorescence Spectroscopy of Biological Tissue", Optical Letters, vol. 25, No. 19. Oct. 1, 2000, pp. 1451-1453.

ved electro-surgical system is of benefit, and has in consequence devised the present invention.

ELECTRO-SURGICAL SYSTEM, AN ELECTRO-SURGICAL DEVICE, AND A METHOD FOR OPERATING AN ELECTRO-SURGICAL SYSTEM

CROSS-REFERENCE TO PRIOR APPLICATIONS

This application is the U.S. National Phase application under 35 U.S.C. §371 of International Application Ser. No. PCT/IB2012/050402, filed on Jan. 16, 2013, which claims the benefit of U.S. application Ser. No. 61/588,748, filed on Jan. 20, 2012. These applications are hereby incorporated by reference herein.

FIELD OF THE INVENTION

The present invention relates to an electro-surgical system with an optical feedback functionality for performing electro-surgery on an associated subject, e.g. a patient. The invention also relates to a corresponding electro-surgical device, a corresponding method for operating an electro-surgical system.

BACKGROUND OF THE INVENTION

In electro-surgery, a high-frequency (HF), alternative called radio frequency (RF), electric current is applied to tissue in order to cut, coagulate, desiccate, and/or fulgurate tissue depending on the mode of delivering electric energy to the tissue. The fact that such a device is used in a large amount of surgical procedures already indicates the usefulness of the electro-surgical device or the electro-surgical unit (ESU), in clinical practice also known as a 'Bovie' device named after the Dr. William T. Bovie, one of the original inventors of the device.

Depending on the tissue in front of the electro-surgical device, the surgeon can decide on which operating mode of the device is used, e.g. cutting and/or coagulating. A problem is however that the surgeon cannot know beforehand what kind of tissue is just below the device since it is typically not visible to the eye. As a result, either the surgeon must decide upfront the mode to be used, or have to react afterwards to what happens with the tissue. For instance, he/she may cause a bleeding and then has to take actions afterwards to stop the bleeding. Another problem is related to complications, thus, when the surgeon is operating, he/she would like to prevent negative influence on critical tissue structures of the patient. Again, the surgeon cannot know beforehand because he/she cannot always predict or determine the tissue structure that lay ahead.

In U.S. Pat. No. 7,749,217, an electro-surgery device is described in which a light delivery system is positioned in the hand piece of the device (see FIG. 1, PRIOR ART). The light delivery system is capable of focusing a beam of light near, or on, the active electro-surgical electrode to detect the amount of blood, and a corresponding control of the electro-surgical energy generator is capable of e.g. automatically changing from a cutting mode to a mixed, or blended, cutting and coagulation mode when detecting a significant amount of blood i.e. a reactive control. Further, the electro-surgical device disclosed in U.S. Pat. No. 7,749,217 has the inherent disadvantage that the light delivery system will typically be rather imprecise due to the remote position on the handle portion. Since most of the detected light is reflected from the surface almost no information of what is tissue is present below the surface can be detected. Also, the light system is only capable of detecting blood.

The inventors of the present invention have appreciated that an improved electro-surgical system is of benefit, and has in consequence devised the present invention.

SUMMARY OF THE INVENTION

It would be advantageous to achieve an improved electro-surgical system. It would also be desirable to enable an improved optical feedback in an electro-surgical system. In general, the invention preferably seeks to mitigate, alleviate or eliminate one or more of the above mentioned disadvantages singly or in any combination. In particular, it may be seen as an object of the present invention to provide a method that solves the above mentioned problems, or other problems, of the prior art.

To better address one or more of these concerns, the invention relates in a first aspect to an electro-surgical system with an optical feedback functionality for performing electro-surgery on an associated subject, the system comprising:

an electro-surgical power source capable of providing a high frequency (HF) signal, an electro-surgical device, the device comprising:

a handling portion, and an electrode portion, the electrode portion being electrically connected to the electro-surgical power source for receiving said high frequency (HF) signal so as to perform electro-surgery upon bringing the electrode portion into contact and/or proximity of said subject, an optical guide, the optical guide being integrated into said electrode portion so that an optical exit position from the optical guide, and/or an optical entry position into the optical guide, are positioned with at least a part of said electrode portion between the handling portion and at least one of said optical entry and exit positions, an optical unit for optical characterization of tissue type and/or condition, the optical unit being optically connected to the optical guide for transmitting optical radiation, and receiving corresponding optical radiation, to and from, respectively, the tissue of the subject, the optical unit comprising:

an optical radiation source capable of emitting radiation, a corresponding spectrometer capable of receiving corresponding radiation from the tissue and further arranged for performing an analysis of the tissue type and/or condition, and a control unit connected to the optical unit, the control unit being capable of generating a feedback control signal based on the analysis of the tissue type and/or condition.

The invention is particularly, but not exclusively, advantageous for obtaining an electro-surgical system where the electrode portion is integrated with an optical guide, the optical guide being coupled to the optical unit for coupling light into the tissue in contact, and/or proximity to the cutting part of the electrode portion, the 'blade electrode', so as to collect reflected light back into the guide, and depending on the optical signal measured in front of the blade electrode, generate a feedback control signal that can be applied in a predictive and/or a proactive feedback to the surgeon using the electro-surgical system.

In particular, the invention is advantageous in that it may enable coupling of light into the tissue in contact, and/or proximity to the cutting part of the electrode portion so as to collect the diffuse scattered light inside the tissue which is reflected back into the guide. Thus the light may propagated into the tissue and has also probed structures deeper below the surface. This is more advantageous over the prior art that mainly detects the reflected light from the surface. If the electro-surgical device is in contact with the tissue it is possible to lower the surface back reflection significantly.

The fact that one or more optical guides are integrated in blade electrode allows inspecting the tissue that is e.g. just a few millimeters ahead of the electrode portion performing e.g. the cutting. As a result of the fast and reliable analysis performed by the spectrometer in the optical unit according to the present invention, the system can proactively react to what kind of tissue is in front of the electro-surgical portion i.e. the 'blade' of the electro-surgical device or the electro-surgical 'knife'. For instance, when an important nerve structure is approached, the electro-surgical system may shut down, or change mode, to prevent cutting it. Another example is when a bigger blood vessels is being approached the device could be switched to a mode that coagulates the blood vessel beforehand before cutting it, and so forth.

Moreover, the advanced analysis of the spectrometer in the present invention also allows for discriminating between various conditions of one kind of tissue, e.g. normal and malign tissue, during the use of electro-surgical system, thus yielding very beneficial assistance to the surgeon when for example removing malign tissue from a patient during a surgical procedure.

It is further worth noting that previously the use of electro-surgical devices, as with conventional scalpels, has been heavily dependent on the skills and experience of the surgeon using them, the present invention may facilitate more easy use by less experienced surgeons due to the predictive feedback facilitated by the present invention, in particular the possibility of automatically preventing cutting of certain kind of tissue may represent a significant advantage with respect to clinical safety.

The active electrode or electrode portion of the electro-surgical device is also known as the 'blade' of the electro-surgical device due to the functional resemblance to a cutting part of a knife. Thus, in present application the electro-surgical active electrode portion delivering at least part of the electric energy to the tissue may interchangeably be called a 'blade'.

In the context of the present invention, the handle portion of the electro-surgical device may be a portion suitable or arranged for holding the device in the hand of a surgeon, i.e. a handle or hand piece. The handle portion may however also be suitable for robotic handling i.e. a portion suitable for attachment on a gripping device of a surgical robot, e.g. the da Vinci® surgical robot system. Preferably, the handle portion is electrically isolated from the electrode portion of the electro-surgical device.

The optical guide applied in the present invention may include an optical guide capable of guiding any kind of electro-magnetic radiation, e.g. infrared radiation, visible light, ultraviolet radiation, X-ray radiation, etc. The optical guide may comprise several sub guides as will be explained in more details below.

Electro-surgery has been known since 1926, and may be broadly defined as the application of high frequency (HF) electrical power in order to cut, coagulate, desiccate, and/or fulgurate the tissue. The HF power may be delivered in various ways depending on frequency, waveforms, voltage, current, etc. as it will be known to the skilled person in electro-surgery. Presently, it is contemplated, without being bound to any specific theory, that the current density is a decisive parameter in a mechanism where the current via Joule heating of the tissue causes an electro-surgical effect. Notice that this is fundamentally different from so-called electro-cautery where the direct current (DC) heating of an electrical conductor is used for heating tissue. Thus, for electro-surgery the heating may be performed within the tissue, not in the electrode portion.

Electro-surgery may be performed in at least two different ways; dipolar where two electrode portions are in contact with the tissue to be impacted, and monopolar where an electrode portion is applied on the tissue of a subject, and a more remote electrode on the subject, e.g. so-called dispersive pads, are used for the return circuit. The present invention may be implemented in both ways.

Tissue may be broadly defined as a cellular organizational level that is intermediate between cells and a whole or complete organism. Notice that blood may be defined as a 'connecting' tissue, even though it has characteristics of a fluid. Similarly, lymphedema liquids and bone may also be considered connecting kinds of tissue.

Advantageously, the feedback control signal may be arranged for providing a feedback to the surgeon while using the electro-surgical system, such as a tactile, audible, and/or visible feedback. Additionally or alternatively, the feedback control signal may communicated to the electro-surgical power source, and, in dependency on an operation mode of the electro-surgical system, the feedback control signal is capable of changing and/or terminating the current operation mode of the electro-surgical system e.g. from cutting to coagulation or other clinically relevant changes.

In an advantageous embodiment, the feedback control signal related to a specific portion of tissue may be generated prior to performing electro-surgical surgery on said specific portion of tissue. Thus, the present invention may be operated in a proactive mode of electro-surgery, e.g. in one mode the electro-surgical system is, to some extent, incapable of performing some no desirable actions, i.e. "foul safe" mode, due to the feedback control signal preventing the electro-surgical generator in performing certain actions, or entering certain modes.

Advantageously, the electrode portion may have an elongated shape with a proximal end nearest the handle portion, and a distal end relative to the handling portion, the optical exit and/or entry positions being positioned at the distal end of the electrode portion. Thus, the electro-surgical system according to the present invention is not per see limited to any specific geometry of the electro-surgical device using the surgery, or configuration for integrating the optical guides together with the electrode portion of the electro-surgical device.

The optical guide according to the present invention may be divided into several optical sub-guides, e.g. individual optical fibers. Alternatively, several optical guides may be applied. Preferably, the optical guide, in particular the optical exit and entry positions, may be equipped with appropriate lenses and other kind of optical components known to the skilled person for performing optical analysis of tissue.

Preferably, the optical guide comprises at least two or three optical sub guides, at least one optical sub guide for transmitting optical radiation for irradiation of tissue, and at least one optical sub guide for receiving optical radiation from the tissue. Beneficially, the optical guide and the optical unit may then be arranged for providing spatial information and/or positions of the tissue relative to the exit and entry positions of the optical guide. Thus with for example three or more optical sub guide (optical fibers) appropriately arranged, a long and short optical path may give simple spatial resolution around the electro-surgical device.

It also enables spatial information to be combined with the feedback signal e.g. increasing sound when a critical blood vessel or nerve is approaching the electro-surgical blade.

More advantageously, the feedback control signal (FEEDCON) may be based on the analysis of the tissue type and/or condition so that it is further dependent on the said spatial information and/or positions of the tissue relative to the exit and entry positions of the optical guide. This may in turn enable direction specific operation of the electro-surgical device, e.g. cutting in a certain direction, and not cutting in other directions relative to the electro-surgical device.

In general, the optical unit for optical characterization of tissue type and/or condition may be based on one, or more, of the optical techniques: diffuse reflectance, fluorescence, Raman, OCT, and multiple photon imaging. Other optical techniques readily available to the skilled person for integration with the present invention are also contemplated. More generally, any optical technique that may perform optical communication through optical guides (integrated with the electro-surgical electrode) may be applied in the context of the present invention.

Advantageously, the optical unit for optical characterization of tissue type and/or condition may be based on diffuse reflectance spectroscopy technique, the exit and entry positions being positioned with sufficient relative distance for diffusive reflectance spectrometry to be performed. Diffusion theory may require a certain minimum inter-distance, otherwise known reference may be used.

It is particular beneficial that the optical guide in the blade is in contact, or close to, the tissue so that the amount of backscattered light which comes from the surface of the tissue is significantly reduced. Light that is scattered into the tissue and probing deeper in the tissue is then detected; this is called "diffuse reflected light" and the technique "diffuse reflectance spectroscopy". The diffuse reflected light contains the information on the tissue below the surface, which is important for analysis.

Advantageously, wherein the optical unit may comprise a dedicated processor and database with tissue specific absorption coefficients etc. for performing tissue type and/or condition analysis.

In one embodiment, the electro-surgical device may further arranged for performing conductivity measurements of tissue, the result of said measurements being communicated to the control unit and applied in generating the feedback control signal for more advanced control and feedback in the system.

In another embodiment, the electro-surgical device may be further arranged for performing optical imaging of tissue through the optical guide, the optical image being communicated to the control unit and applied in generating the feedback control signal for more advanced control and feedback in the system.

In a second aspect, the present invention relates to an electro-surgical device for application in an electro-surgical system with an optical feedback functionality for performing electro-surgery on an associated subject, the device comprising:
a handling portion, and
an electrode portion, the electrode portion being arranged for electrically connection to an electro-surgical power source for receiving said high frequency (HF) signal so as to perform electro-surgery upon bringing the electrode portion into contact and/or proximity of said subject, and
an optical guide, the optical guide being integrated into said electrode portion so that an optical exit position from the optical guide, and/or an optical entry position into the optical guide, are positioned with at least a part of said electrode portion between the handling portion and at least one of said optical entry and exit positions, In a third aspect, the present invention relates to a method for operating an electro-surgical system with an optical feedback functionality for performing electro-surgery on an associated subject, the method comprising:
providing an electro-surgical power source capable of providing a high frequency (HF) signal,
providing an electro-surgical device, the device comprising:
a handling portion, and
an electrode portion, the electrode portion being electrically connected to the electro-surgical power source for receiving said high frequency (HF) signal so as to perform electro-surgery upon bringing the electrode portion into contact and/or proximity of said subject,
an optical guide, the optical guide being integrated into said electrode portion so that an optical exit position from the optical guide, and/or an optical entry position into the optical guide, are positioned with least a part of said electrode portion between the handling portion and at least one of said optical entry and exit positions,
providing an optical unit for optical characterization of tissue type and/or condition, the optical unit being optically connected to the optical guide for transmitting optical radiation, and receiving corresponding optical radiation, to and from, respectively, the tissue of the subject, the optical unit comprising:
an optical radiation source capable of emitting radiation,
a corresponding spectrometer capable of receiving corresponding radiation from the tissue and further arranged for performing an analysis of the tissue type and/or condition, and
providing a control unit connected to the optical unit, the control unit being capable of generating a feedback control signal (FEEDCON) based on the analysis of the tissue type and/or condition.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
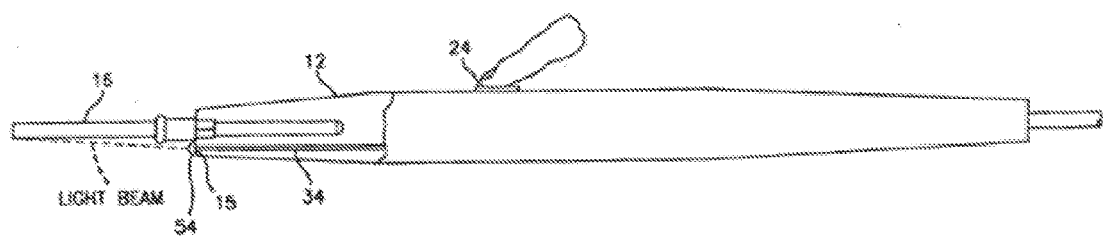
FIG. 1 is a prior art example of an electro-surgical device from U.S. Pat. No. 7,749,217.

FIG. 1 is a prior art example of an electro-surgical device from U.S. Pat. No. 7,749,217, in which a light delivery system is positioned in the handpiece 12 of the device. The light delivery system is capable of focusing a beam of light near, or on, the active electro-surgical electrode 16 to detect the amount of blood, and a corresponding control of the electro-surgical energy generator (not shown) is capable of automatically changing from e.g. a cutting mode to a mixed, or blended, cutting and coagulation mode when detecting a significant amount of blood i.e. a reactive control of electro-surgical device.

Figure 2:
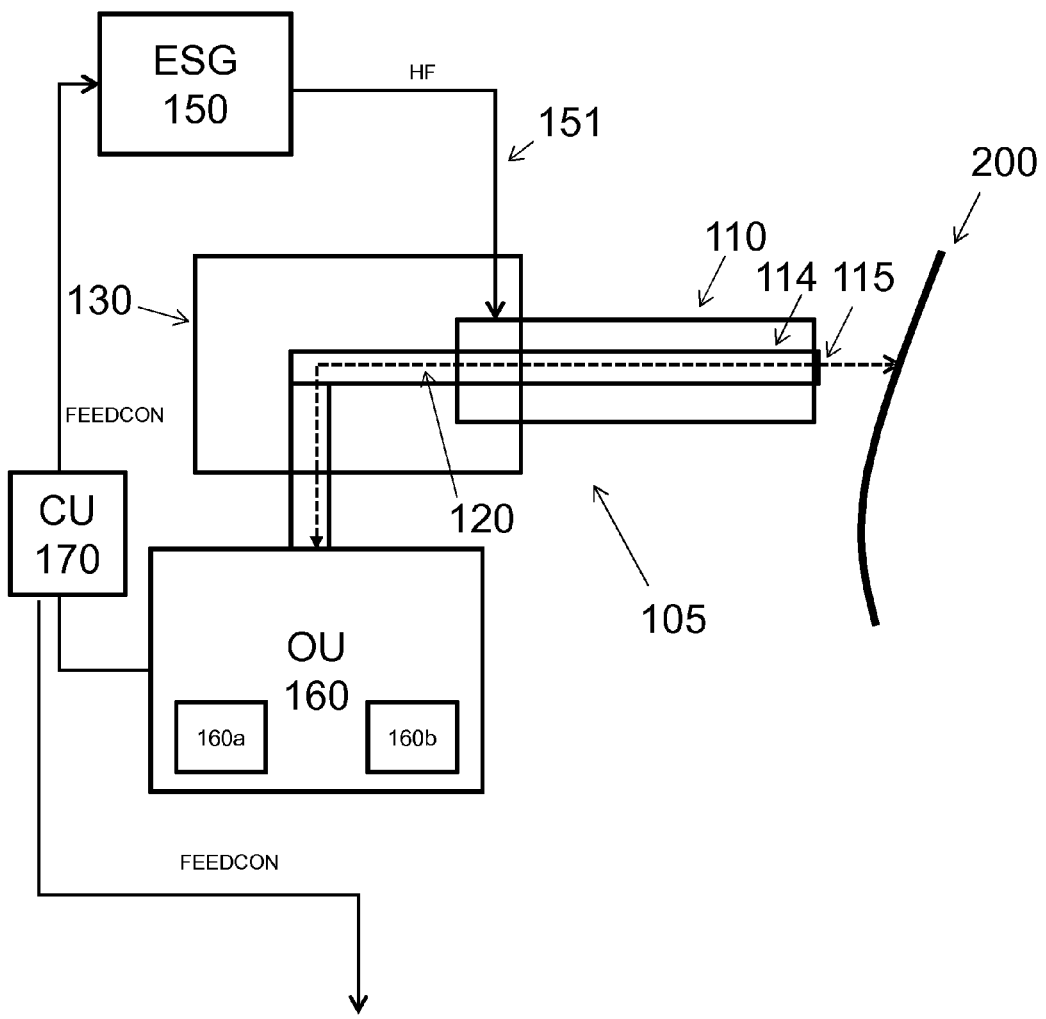
FIG. 2 is schematic illustration of an electro-surgical system according to the present invention.

FIG. 2 is schematic illustration of an electro-surgical system 100 according to the present invention. The electro-surgical system 100 has an optical feedback functionality for performing electro-surgery on tissue 200 of an associated subject. The system comprises an electro-surgical power source 150 capable of providing a high frequency (HF) signal for electro-surgery.

Furthermore, an electro-surgical device 105 with comprises a handling portion 130 for handling by a surgeon or a robotic device (neither shown), and an electrode portion 110, the electrode portion being electrically connected, as indicated with arrow 151, to the electro-surgical power source ESG 150 for receiving said high frequency HF signal so as to perform electro-surgery upon bringing the electrode portion 110 into contact and/or proximity of said subject 200.

Additionally, the electro-surgical device has an optical guide 114, the optical guide being integrated into said electrode portion so that an optical exit and exit position 115 from the optical guide are positioned with least a part of said electrode portion between the handling portion and said optical entry and exit position. In this configuration, the optical exit and entry position are the same, but other configuration with will be shown below where this is not the case.

An optical unit 160 for optical characterization of tissue type and/or condition is optically connected to the optical guide for transmitting optical radiation and receiving corresponding optical radiation, to and from, respectively, as indicated with double dashed arrow 120, the tissue 200 of the subject. The optical unit comprises an optical radiation source 160b capable of emitting radiation, and a corresponding spectrometer 160b capable of receiving corresponding radiation from the tissue and further arranged for performing an analysis of the tissue type and/or condition, as will be explained in more detail below.

Further, the electro-surgical system comprises a control unit 170 connected to the optical unit 160, the control unit being capable of generating a feedback control signal FEEDCON based on the analysis of the tissue type and/or condition. In FIG. 2, the signal FEEDCON is shown as being applied in control of the electro-surgical generator 150, e.g. the feedback loop can automatically selects the operating mode of the electrical generator 150.

Figure 3A:
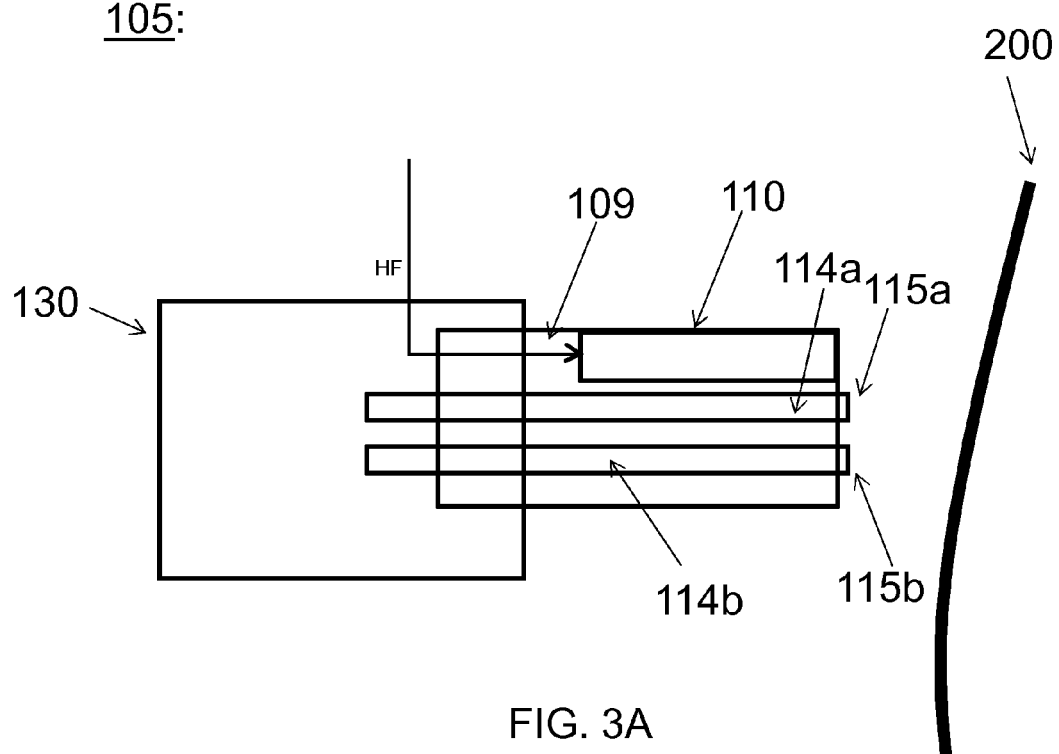
FIG. 3 is a schematic illustration of an electro-surgical device to according to the present invention.

In FIG. 3A, an embodiment of the electro-surgery device 105 according to the invention is shown in a schematic cross-sectional view. The electro-surgery device 105 consists of a blade or extension 109 with an electrode portion 110 attached thereon, the blade or extension having two light guides 114a and 114b integrated into the blade 109 and the electrode portion as shown. The light guides 114 are connected to the optical console 160 (not shown in FIG. 3). The electrode 110 is electrically connected to the electrical console 150 capable of sending electrical signal to the blade inducing various treatments such as to cut, coagulate, desiccate, or fulgurate tissue. The electrode 110 is capable of performing these treatments to the tissue 200. The electro-surgical device 105 thus comprises a handle portion 130, an extension 109 whereupon an electrode portion 110 is integrated with optical guide 114, the optical exit and entry positions 115 having at least the left part of the electrode portion positioned between the handle portion 130 and positions 150, alternatively worded; the part of the electrode 110 being closest to the handle portions 130 is closer to the handle portion 130 than the optical exit and entry positions 115 as measured by direct physical distance, or in a projection along the electro-surgical device 105.

Figure 3B:
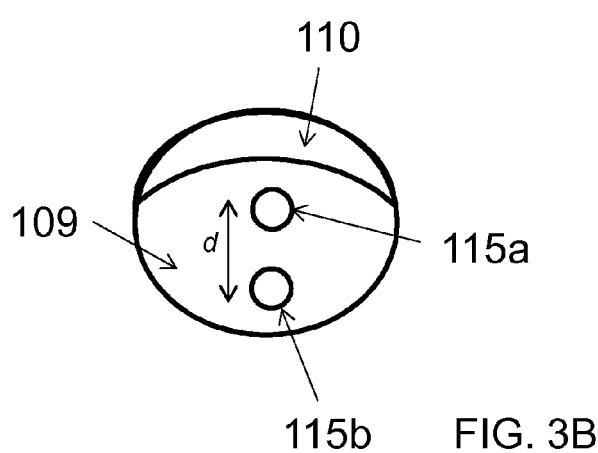

In a frontal view FIG. 3B of this embodiment, the optical exit 114a and entry 114b position is shown together with the electrode portion 110 covering a peripheral part of a circular shape of the extension 109. The distance d between the optical exit and entry positions 115 is important for diffusive reflectance spectrometry because this distance determines the accuracy and also the spatial depth of the area probed by diffusive reflection spectrometry, roughly a depth of d/2 is probed. The electro-surgical device 105 may have other shapes, as seen in frontal view, e.g. rectangular, quadratic, elliptic, etc., depending on the surgical application and conditions. Furthermore, the electrode portion 110 may cover all or only a part of the peripheral part of the electro-surgical device 105. Alternatively, the electrode portion 110 may complete cover the extension 109, only leaving dedicated small holes to the optical exit and entry positions 115. Even more alternatively, the optical exit and entry positions 115 may be transmitted through a conducting transparent materials, e.g. conducting glass or optical transparent metals, enabling the electrode portion 110 to completely cover the extension 109 connected to the handle portion 130.

According to a preferred embodiment of the invention, one of the light guides 114a is connected to a light source in the optical console 160 illuminating the tissue in contact with the blade 110. Scattered light that has travelled through the tissue 200 in contact with the blade 110 is collected by a second light guide 114b and directed towards the optical unit 160, cf. FIG. 2. Here the light is spectrally analysed. From the spectral signatures the tissue type and/or condition in front of the electrode portion 110 can be determined. For instance using a white light source and detecting the diffuse reflected light it is possible to detect the presence and concentration of various chromophores such as water, lipid blood, blood oxygenation, bile, beta-carotene etc. These parameters are then used to identify the tissue such a nerve tissue, blood vessel, muscle tissue etc. A way to analyse this is described in the references;

J. Farrel, M. S. Patterson and B. C. Wilson, "*A diffusion theory model of spatially resolved, steady-state diffuse reflectance for the non-invasive determination of tissue optical properties,*" Med. Phys. 19 (1992) p879-888.

R. Nachabé, B. H. W. Hendriks, A. E. Desjardins, M. van der Voort, M. B. van der Mark, and H. J. C. M. Sterenborg, "*Estimation of lipid and water concentrations in scattering media with diffuse optical spectroscopy from 900 to 1600 nm*", J. Biomed. Opt. 15, 037015 (2010).

Rami Nachabé, Benno H. W. Hendriks, Marjolein van der Voort, Adrien E. Desjardins, and Henricus J. C. M. Sterenborg, "*Estimation of biological chromophores using diffuse optical spectroscopy: benefit of extending the UV-VIS wavelength range to include 1000 to 1600 nm*", Optics Express 18 (2010) p1432.

Rami Nachabé, Daniel J. Evers, Benno H. W. Hendriks, Gerald W. Lucassen, Marjolein van der Voort, Jelle Wesseling, and Theo J. M. Ruers, "*Effect of bile absorption coefficients on the estimation of liver tissue optical properties and related implications in discriminating healthy and tumorous samples*", Biomedical Optics Express 2 (2011) p600.

Also fluorescence detection can be used to determine tissue composition, see hang et al., Optics Letters 25 (2000) p1451.

All of the above references are incorporated by reference in there entirety.

A mode selecting switch (not shown) can be present on the handle portion 130 to select different operating mode depending on the signal identified by the optical console 160.

FIGS. 4-7 are schematic illustrations of various electro-surgical devices to according to the present invention similar to the variant shown in FIG. 3.

Figure 4A:
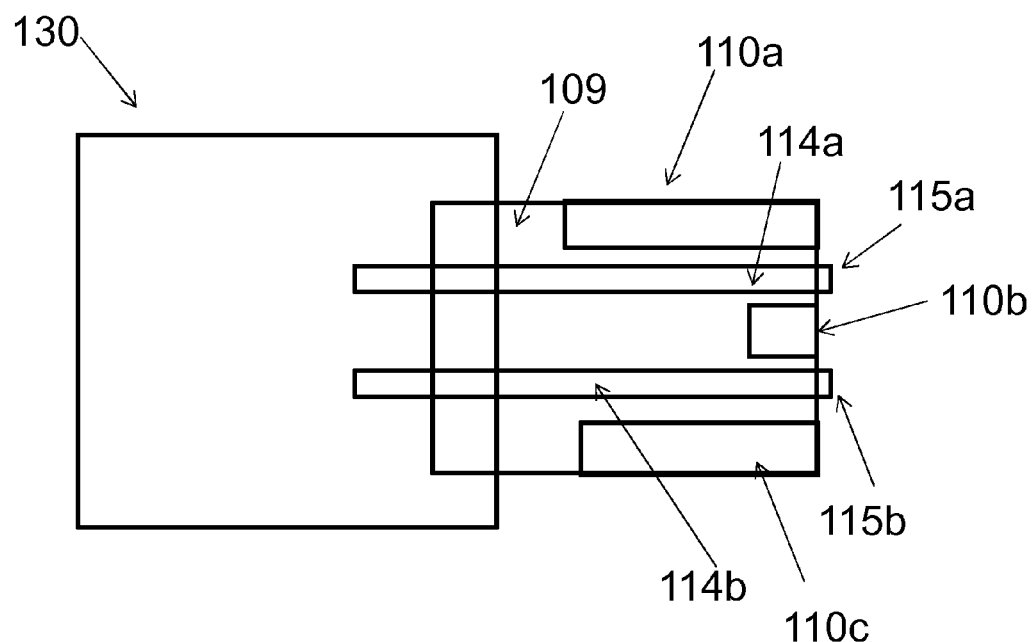
FIGS. 4-7 are schematic illustrations of various electro-surgical devices to according to the present invention.
Figure 4B:
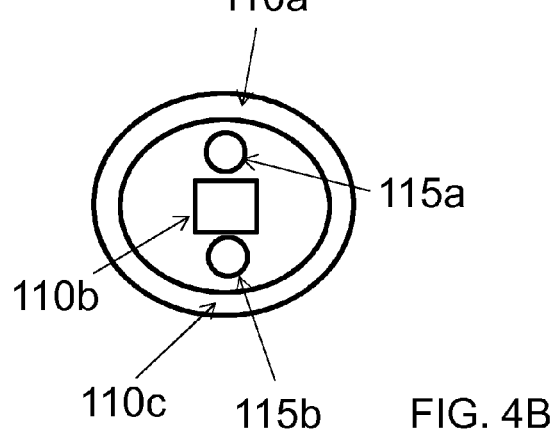

In FIG. 4, the electrode portions 110 cover the entire periphery of the extension 109 as seen in frontal view of FIG. 4B. In addition, an electrode portion 110b is positioned in central position. The electrode portion 110b may be at another potential relative to the peripheral electrode portion 110a, 110c, e.g. in bipolar electro-surgery.

The present invention may generally be implemented with two, three, four, five or more electrodes, each being independently controllable or collectively controllable as the design specification or surgical condition requires.

In this embodiment, the fibers or optical sub guides 114 used in the device 105 have a metal buffer. The buffer gives on the one hand the protection for the fibers from being damaged due to the heat produced by the electro-surgery, while on the other hand it can serve as the electrical connection. Furthermore, the metal buffer may also be used to mount the fibers in the extension 109 by using soldering or welding instead of glueing. When more than one optical sub guide 114 is integrated into the extension 109, the electrical resistance measurements between the metal buffers can be used to select the fibers to be used. It is also possible to segment the metal part of the blade such that even directional cutting is possible.

Figure 5A:
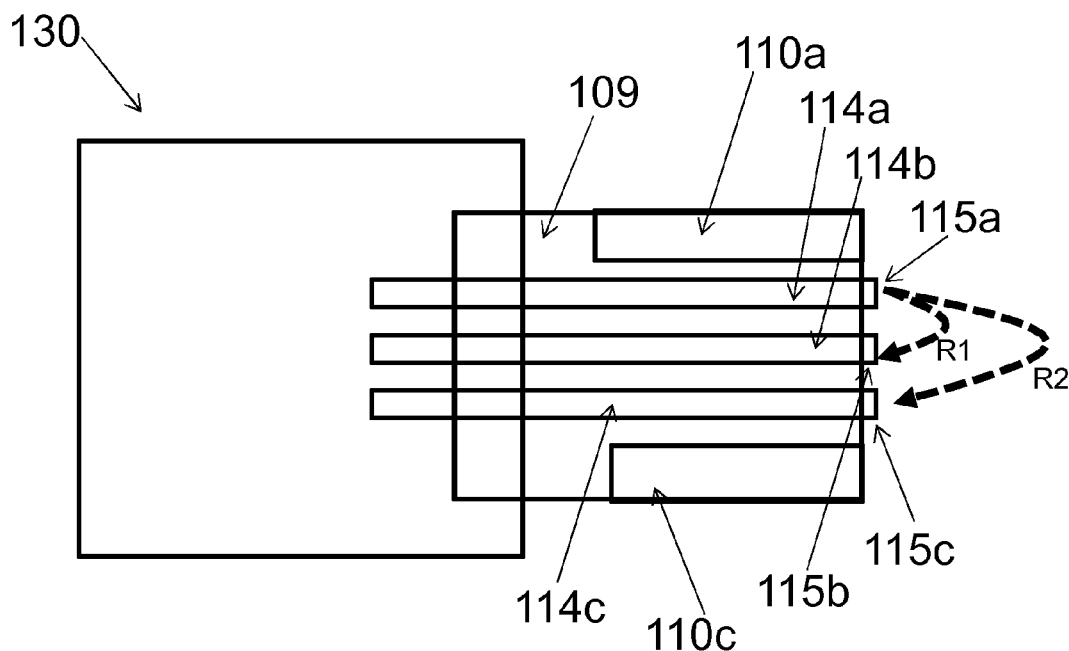
Figure 5B:
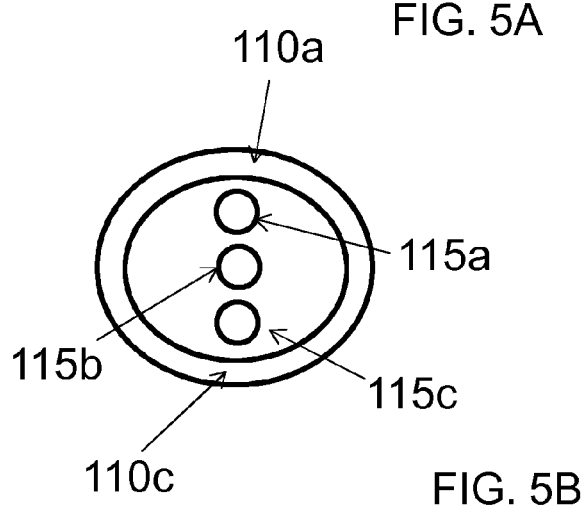

In FIG. 5, another embodiment has the presence of three light sub guides 114a, 114b, 114c, with corresponding optical exit and entry positions 115a, 115b, 115c, respectively, that can be used to detect and circumvent artefacts in tissue characterization arising from operating the blade electrode in tissue. Electro-surgical treatment may alter the optical properties of the tissue in close vicinity of the blade electrode and thereby affect tissue discrimination. For instance, the water content of the local tissue environment is typically vaporized during operation, with the extent of vaporization depending on the operating mode (such as cutting, coagulation, desiccation, fulguration), If two light guides are present, as in FIGS. 3 and 4, the influence of artefacts in optical tissue characterization can be circumvented by choosing the fiber distance d sufficiently large so that the probed volume is at a sufficiently large distance d/2 ahead of the blade and therefore does not contain significant contributions from the currently treated tissue in the vicinity of the blade. For this case, d should be chosen large enough to ensure the minimization of artefacts for all available operating modes (such as cutting, coagulation, desiccation, fulguration).

If more than two light guides are present, as in this embodiment of FIG. 5, different volumes can be probed at different distances in front of the blade. In this case, possible effects of treatment on the optical signal are not considered an artefact but rather an additional source of information that may help the physician to decide whether the treatment on the current spot has to be continued or can be stopped.

For instance, it allows for monitoring the progress of treatment in a volume traversed by radiation R1 (bold dashed arrow exiting from exit position 115a, entering entry position 115b) close to the blade, with the optical signal changing during the treatment. At the same time, a tissue volume traversed by radiation R2 (bold dashed arrow exiting also from exit position 115a, but entering entry position 115c) further away from the electrode portion 110 is not, or not significantly, affected by the treatment and gives information from the untreated tissue nearby. This allows the physician to decide when and where to continue the treatment in nearby tissue and/or to switch to a different operation mode if necessary.

Figure 6A:
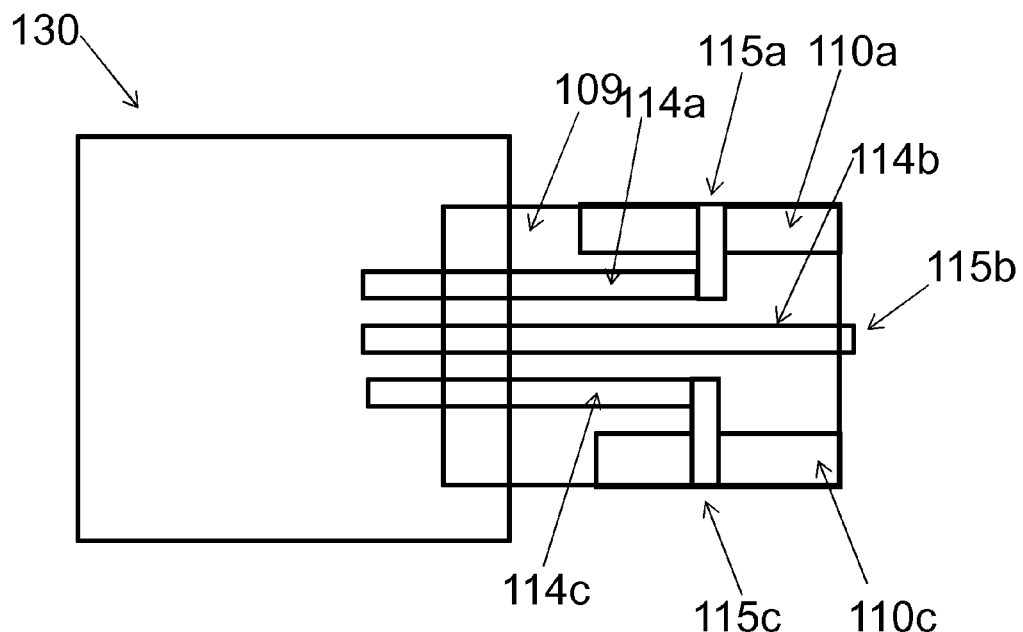
Figure 6B:
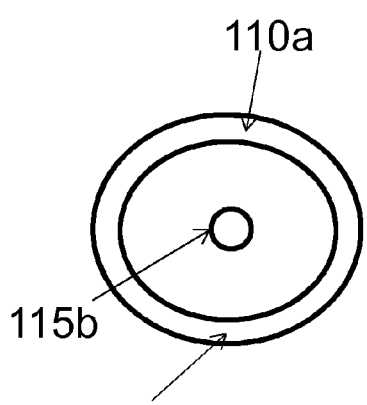
Figure 6C:
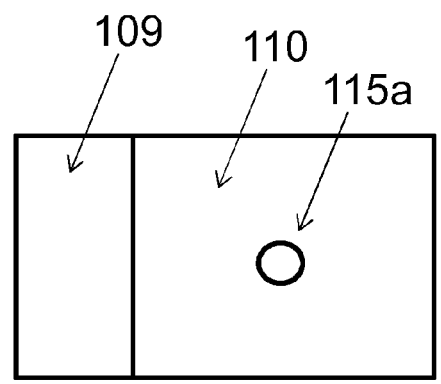

In FIG. 6, which is similar to the embodiment of FIG. 5 with three optical sub guides, there is a different configuration of the optical guides, thus in this embodiment optical sub guides 114a and 114c are directed in a sideways position relative to the elongated extension 109 with the electrode portion 110a and 110c. Thus, in the top view of FIG. 6C as of the extension 109 the optical sub guide 114a ends in optical position 115a penetrating the electrode portion 110 as shown schematically. This will be enable spatial and directional information to be retrieved from the optical analysis by diffusively reflective spectrometry, e.g. by exiting optical radiation from optical end position 115b and re-entering via reflectively scattering into optical entry positions 115a and 115c. In this embodiment, the various light sub guide distal ends are at different location of the electro portion 110 such that an orientation detection of tissue structure becomes possible. For instance when light guide pairs are positioned at opposite positions of the extension 109 it can be inferred from which side the structure is approached by the electro-surgical electrode portion 110.

Figure 7A:
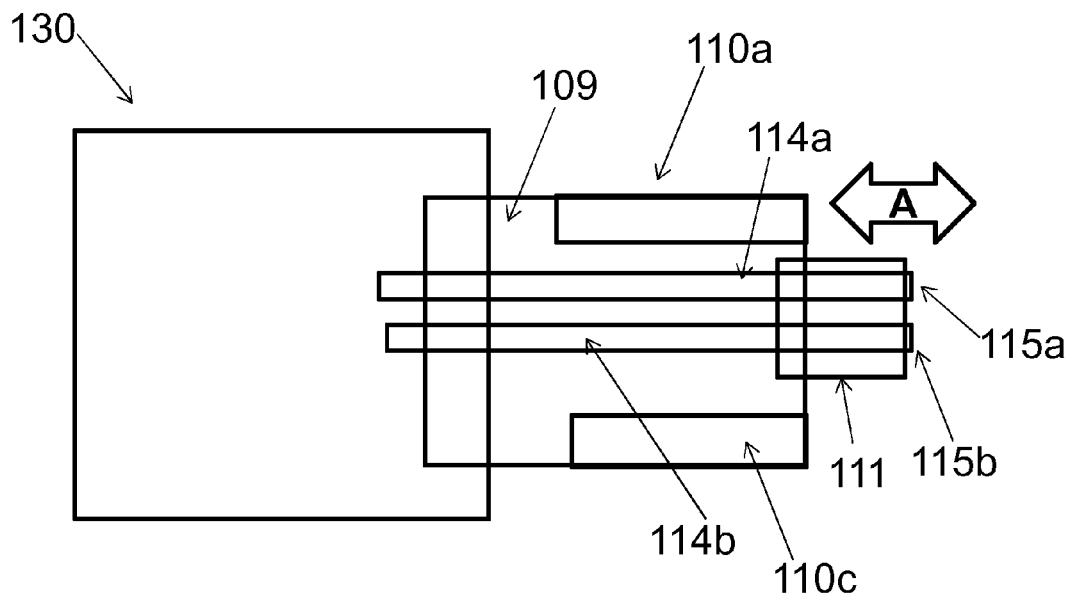
Figure 7B:
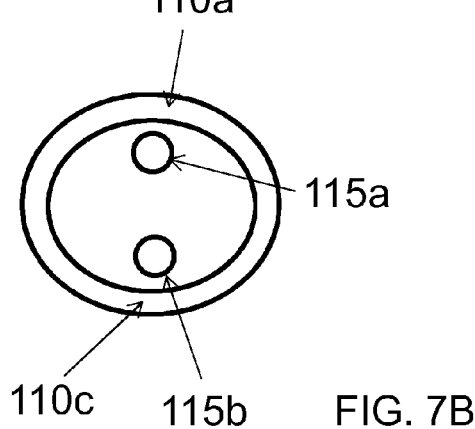

In FIG. 7, yet another embodiment is shown with the electro-surgical device 105 comprising a top portion 111 of the extension 109 being displaceable together with the optical exit and entry positions 115 as indicated with double arrow A. Thus, the optical sub guides 114 are flexible or extendable, too. Thus, the electrode 110 can be combined with an integrated, non-conducting and sharp top part 111 containing at two, or more, light guides 114a and 114b for optical tissue characterization ahead of the blade electrode 110.

For instance, a needle-like top portion or top piece 111 made of non-conducting material with two light guides 114a and 114b can be used for puncturing into the tissue 200 (not shown) in front of the electrode portion or 'blade' 110, and for optical characterization of the tissue volume. The protrusion of the top piece 111 can be chosen with a sufficient distance between the electrode 110 and the end of the light guides 115 to allow for characterizing the tissue in front of the blade without the influence of treatment artefacts that may arise in close vicinity of the blade electrode 110.

One advantage of this design is that when the electrode portion or blade 110 is moved forward during operation, the device offers the possibility to probe the untreated tissue at a certain distance in front of the approaching blade, allowing the physician to make a decision on how to proceed with the treatment.

The top piece 111 can also be designed in way that allows for adjusting its protrusion from the blade 110 and thereby the distance between the blade electrode and the end of the light guides. The physician can choose the distance which is most suited for the current treatment method and tissue type. This embodiment extends the capability of the device to probe untreated tissue volumes at multiple distances in front of the blade electrode.

In the embodiment of FIG. 7, the protrusion of the top portion 111 is schematically depicted as a forward linear displacement as indicated by double-arrow A, but other displacements, e.g. pivotal displacement or sideward displacement are also envisioned.

Figure 8:
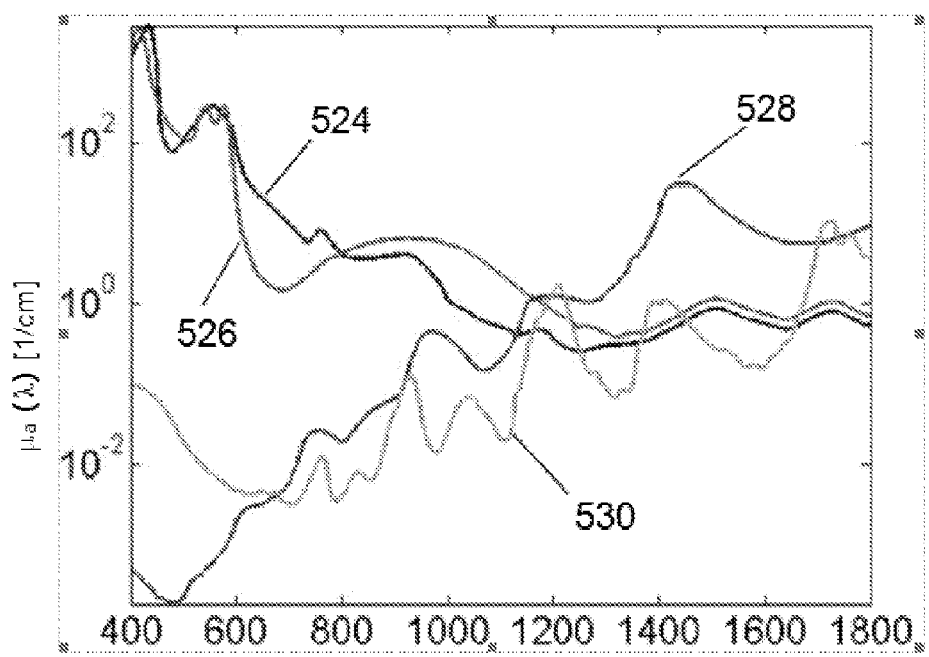
FIG. 8 shows absorption spectra of some of the most important chromophores present in the human body namely blood, water and lipid.

FIG. 8 shows absorption spectra of some of the most important chromophores present in the human body namely blood, water and lipid, to be applied in the below algorithm; deoxygenated haemoglobin (Hb) 524, oxygenated haemoglobin (HbO2) 526, water 528 and lipid 530, are shown as a function of the wavelength.

In the following an algorithm for extracting information from reflectance spectroscopy spectra is described. The inventors of the present application have participated in developing an algorithm that can be used to derive optical tissue properties such as the scattering coefficient and absorption coefficient of different tissue chromophores: e.g. hemoglobin, oxygenated haemoglobin, water, lipid, collagen and elastin from the reflectance spectra. These properties may be different between normal and pathologic tissues. Based on this knowledge is possible to discriminate between various kind of tissue and/or discriminate between various condition of a tissue. The present inventors has developed this algorithm so that sufficient certain and quick optical analysis can be performed in context of performing electro-surgery with an electro-surgical system as described in the present application.

The spectral fitting will be performed by making use of an analytically derived formula for reflectance spectroscopy which has recently been described in a scientific article featuring the some of the inventors of the present application as authors "*Estimation of lipid and water concentrations in scattering media with diffuse optical spectroscopy from 900 to 1600 nm*", Nachabé et al., Journal of Biomedical Optics 15(3), 1 (May/June 2010), the article is hereby incorporated by reference in its entirety and hereafter referred to as [Nachabé2010a]Another scientific article by the present authors is given by "*Estimation of biological chromophores using diffuse optical spectroscopy: benefit of extending the UV-VIS wavelength range to include 1000 to 1600 nm*", R. Nachabé et al., Optics Express 18, 1432-1442 (2010), the article is hereby incorporated by reference in entirety and hereafter referred to as.

The diffuse reflectance model is described in section 2 of [Nachabé2010a], more particularly in section 2.3. The reflectance distribution R is given by $$R(\rho) = \int_0^\infty R(\rho, z_0)\delta(z_0 - 1/\mu_t')dz_0 \quad (1)$$
$$= \frac{d}{4\pi}\left[\frac{1}{\mu_t'}\left(\mu_{eff} + \frac{1}{\tilde{r}_1}\right)\frac{e^{-\mu_{eff}\tilde{r}_1}}{\tilde{r}_1^2} + \left(\frac{1}{\mu_t'} + 2z_b\right)\left(\mu_{eff} + \frac{1}{\tilde{r}_2}\right)\frac{e^{-\mu_{eff}\tilde{r}_2}}{\tilde{r}_2^2}\right]$$

where $\tilde{r}_1 = [\rho^2 + (1/\mu_t')^2]^{1/2}$ $\tilde{r}_2 = [\rho^2 + ((1/\mu_t') + 2z_b)^2]^{1/2}$ $\mu_{eff} = \sqrt{3\mu_a[\mu_a + \mu_s(1-g)]}$ In this formula the three macroscopic parameters describing the probability of interaction with tissue are: the absorption coefficient $\mu_a$ and the scattering coefficient $\mu_s$ both in $cm^{-1}$ as well as by g which is the mean cosine of the scattering angle. Furthermore, the total reduced attenuation coefficient $\mu_t'$ that gives the total chance for interaction with tissue is given by $$\mu_t' = \mu_a + \mu_s(1-g). \quad (2)$$

The albedo a' is the probability of scattering relative to the total probability of interaction $$a' = \mu_s/\mu_t'. \quad (3)$$

we assume a point source at a depth $z_0 = 1/\mu_t'$ and no boundary mismatch hence $z_b = 2/(3\mu_t')$. To simplify some equations we introduce the reduced scattering coefficient $\mu_s'$, which is defined as:

$$\mu_s' = \mu_s(1-g). \quad (4)$$

The person skilled in the art will realize that the choice of which scattering coefficient to choose (the reduced scattering coefficient $\mu_s'$ or the traditional scattering coefficient $\mu_s$) is mainly a matter of convenience, since one can easily be transferred into the other (using a reasonable guess or calculation for g). So henceforward it should be understood the any operation involving $\mu_s$ can also be done with $\mu_s$ and vice-versa.

Furthermore, we assume that the reduced scattering coefficient can be written as $$\mu_s'(\lambda) = a\lambda^{-b}. \quad (5)$$

where $\lambda$ is the wavelength and a and b fixed parameters.

The main absorbing constituents in normal tissue dominating the absorption in the visible and near-infrared range are blood (i.e. hemoglobin), water and lipid.

The total absorption coefficient is a linear combination of the absorption coefficients of chromophores in a probed sample, for instance blood, water and lipid as depicted in FIG. 8. Blood dominates the absorption in the visible range, while water and fat dominate in the near infrared range.

For each component the value of that shown in FIG. 8 must be multiplied by its volume fraction. By fitting the above formula while using the power law for scattering it is possible to determine the volume fractions of chromophores present, for example blood, water, lipid, collagen and elastin as well as the scattering coefficient. With this method it is thus possible to translate the measured spectra in physiological parameters that can be used, e.g., to discriminate different tissues.

It is noted that the measurement of data representative of optical spectra of the associated tissue 200 can be carried out in various ways, such as by means of various filter systems in different positions of the optical path, one or more light sources 160a emitting in one or more delimited wavelength bands, or spectrometers (comprising detectors) for different delimited wavelength bands or the detectors being applicable for different delimited wavelength bands. This is understood to be commonly known by the skilled person. It is also possible to modulate the various wavelength bands with different modulation frequencies at the source and demodulate these at the detector, (this technique is described in the published patent application WO2009/153719 which is hereby incorporated by reference in its entirety). Various other modifications can be envisioned without departing from the scope of the invention for instance using more than one spectrometer 160b comprising one or more detectors or using more than one light source with different wavelength band, such as Light Emitting Diodes (LEDs) or LASER sources.

FIG. 8 thus shows absorption spectra of some of the most important chromophores present in the human body namely blood, water and lipid. The graph shows absorption coefficients of deoxygenated haemoglobin (Hb) 524, oxygenated haemoglobin (HbO2) 526, water 528 and lipid 530 as a function of the wavelength. Note that blood dominates the absorption in the visible range, while water and lipids dominate in the near infrared range. The graph has on its first, horizontal axis, the wavelength (λ, lambda) given in nanometer (nm), and on its second, vertical axis, the absorption coefficient $\mu_a$ (mu_a) given in reciprocal centimetres (1/cm).

Figure 9:
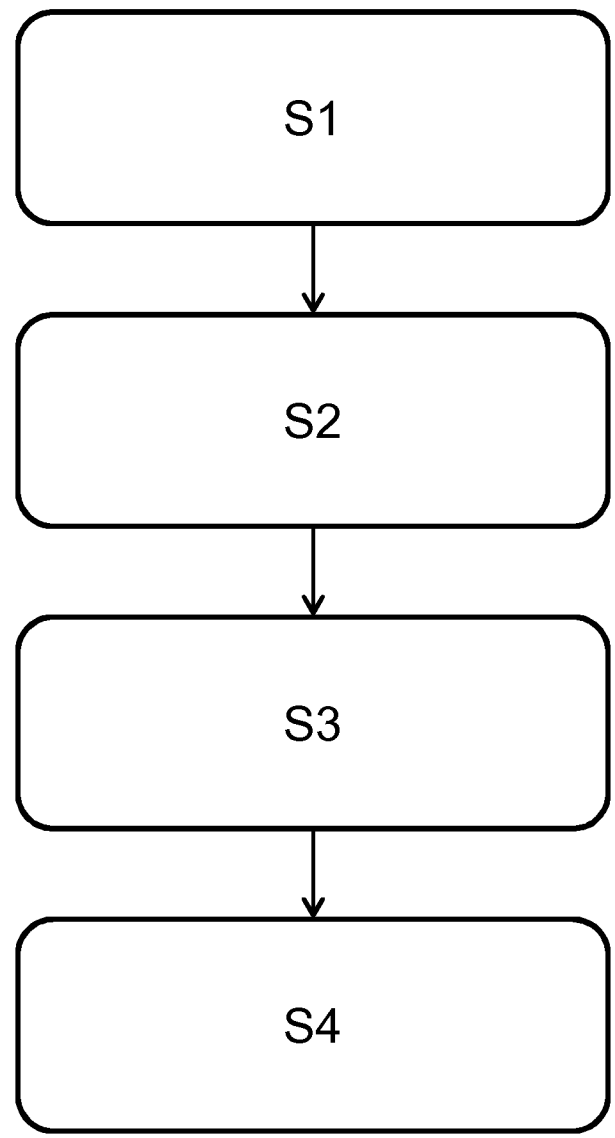
FIG. 9 is a flow chart of method according to the present invention.

FIG. 9 is a flow chart of method according to the present invention for operating an electro-surgical system 100 with an optical feedback functionality for performing electro-surgery on an associated subject, the method comprising:

S1 providing an electro-surgical power source 150 capable of providing a high frequency (HF) signal, S2 providing an electro-surgical device 105, the device comprising:
  a handling portion 130, and
  an electrode portion 110, the electrode portion being electrically connected to the electro-surgical power source for receiving said high frequency (HF) signal so as to perform electro-surgery upon bringing the electrode portion into contact and/or proximity of said subject,
  an optical guide 114, the optical guide being integrated into said electrode portion so that an optical exit position 115a from the optical guide, and/or an optical entry position 115b into the optical guide, are positioned with least a part of said electrode portion between the handling portion and at least one of said optical entry and exit positions, S3 providing an optical unit 160 for optical characterization of tissue type and/or condition, the optical unit being optically connected to the optical guide for transmitting optical radiation 120, and receiving corresponding optical radiation, to and from, respectively, the tissue of the subject, the optical unit comprising:
  an optical radiation source 160a capable of emitting radiation,
  a corresponding spectrometer 160b capable of receiving corresponding radiation from the tissue and further arranged for performing an analysis of the tissue type and/or condition, and S4 providing a control unit 170 connected to the optical unit, the control unit being capable of generating a feedback control signal FEEDCON based on the analysis of the tissue type and/or condition.

In short, the present invention relates to an electro-surgical system 100 with an optical feedback functionality for performing electro-surgery on tissue 200 of patient. An electro-surgical device 105 has an electrode portion 110 with an optical guide 114 integrated therein. An optical unit 160 performs optical characterization of tissue type and/or condition, and is arranged for performing an analysis of the tissue type and/or condition. A control unit 170 generates a feedback control signal FEEDCON based on the analysis of the tissue type and/or condition. optical guide allows inspecting the tissue that is e.g. just a few millimeters ahead of the electrode portion 110 performing e.g. the cutting. As a result of the fast and reliable analysis performed by the spectrometer in the optical unit according to the present invention, the system can proactively react to what kind of tissue is in front of the electro-surgical portion i.e. the 'blade' of the electro-surgical device or the electro-surgical 'knife'.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An electro-surgical system (100) with an optical feedback functionality for performing electro-surgery on an associated subject, the system comprising:
  an electro-surgical power source (150) capable of providing a high frequency (HF) signal,
  an electro-surgical device (105), the device comprising:
    a handling portion (130), and
    an electrode portion (110), the electrode portion being electrically connected to the electro-surgical power source for receiving said high frequency (HF) signal so as to perform electro-surgery upon bringing the electrode portion into contact and/or proximity of said subject, and
    an optical guide (114), wherein the optical guide comprises at least two or three optical sub guides, at least one optical sub guide for transmitting optical radiation for irradiation of tissue, and at least one optical sub guide for receiving optical radiation from the tissue, the optical guide being integrated into said electrode portion so that an optical exit position (115a) from the optical guide, and/or an optical entry position (115b) into the optical guide, are positioned with at least a part of said electrode portion between the handling portion and at least one of said optical entry and exit positions,
  an optical unit (160) for optical characterization of tissue type and/or condition based on diffuse reflectance spectroscopy technique, the exit and entry positions being positioned with sufficient relative distance for diffusive reflectance spectrometry to be performed, the optical unit being optically connected to the optical guide for transmitting optical radiation (120), and receiving corresponding optical radiation, to and from, respectively, the tissue of the subject, the optical unit comprising:
    an optical radiation source (160a) capable of emitting radiation,
    a corresponding spectrometer (160b) capable of receiving corresponding radiation from the tissue and further arranged for performing an analysis of the tissue type and/or condition, and a control unit (170) connected to the optical unit, the control unit being capable of generating a feedback control signal (FEEDCON) based on the analysis of the tissue type and/or condition.

2. The electro-surgical system according to claim 1, wherein the feedback control signal is arranged for providing a feedback to the surgeon while using the electro-surgical system, such as a tactile, audible, and/or visible feedback.

3. The electro-surgical system according to claim 1, wherein the feedback control signal is communicated to the electro-surgical power source, and, in dependency on an operation mode of the electro-surgical system, the feedback control signal is capable of changing and/or terminating the current operation mode of the electro-surgical system.

4. The electro-surgical system according to claim 1, wherein the feedback control signal related to a specific portion of tissue is generated prior to performing electro-surgical surgery on said specific portion of tissue.

5. The electro-surgical system according to claim 1, wherein the electrode portion has an elongated shape with a proximal end nearest the handle portion, and a distal end relative to the handling portion, the optical exit and/or entry positions being positioned at the distal end of the electrode portion.

6. The electro-surgical system according to claim 1, wherein the optical guide and the optical unit are arranged for providing spatial information and/or positions of the tissue relative to the exit and entry positions of the optical guide.

7. The electro-surgical system according to claim 6, wherein the feedback control signal (FEEDCON) based on the analysis of the tissue type and/or condition is further dependent on the said spatial information and/or positions of the tissue relative to the exit and entry positions of the optical guide.

8. The electro-surgical system according to claim 1, wherein the optical unit for optical characterization of tissue type and/or condition is based on one, or more, of the optical techniques: diffuse reflectance, fluorescence, Raman, OCT, and multiple photon imaging.

9. The electro-surgical system according to claim 1, wherein the optical unit comprises a dedicated processor and database with tissue specific absorption coefficients for performing tissue type and/or condition analysis.

10. The electro-surgical system according to claim 1, wherein the electro-surgical device is further arranged for performing conductivity measurements of tissue, the result of said measurements being communicated to the control unit and applied in generating the feedback control signal.

11. The electro-surgical system according to claim 1, wherein the electro-surgical device is further arranged for performing optical imaging of tissue through the optical guide, the optical image being communicated to the control unit and applied in generating the feedback control signal.

12. A method for operating an electro-surgical system (100) with an optical feedback functionality for performing electro-surgery on an associated subject, the method comprising:

providing an electro-surgical power source (150) capable of providing a high frequency (HF) signal, providing an electro-surgical device (105), the device comprising:

a handling portion (130), and an electrode portion (110), the electrode portion being electrically connected to the electro-surgical power source for receiving said high frequency (HF) signal so as to perform electro-surgery upon bringing the electrode portion into contact and/or proximity of said subject, an optical guide (114), wherein the optical guide comprises at least two or three optical sub guides, at least one optical sub guide for transmitting optical radiation for irradiation of tissue, and at least one optical sub guide for receiving optical radiation from the tissue, the optical guide being integrated into said electrode portion so that an optical exit position (115a) from the optical guide, and/or an optical entry position (115b) into the optical guide, are positioned with least a part of said electrode portion between the handling portion and at least one of said optical entry and exit positions, providing an optical unit (160) for optical characterization of tissue type and/or condition based on diffuse reflectance spectroscopy technique, the exit and entry positions being positioned with sufficient relative distance for diffusive reflectance spectrometry to be performed, the optical unit being optically connected to the optical guide for transmitting optical radiation (120), and receiving corresponding optical radiation, to and from, respectively, the tissue of the subject, the optical unit comprising:

an optical radiation source (160a) capable of emitting radiation, a corresponding spectrometer (160b) capable of receiving corresponding radiation from the tissue and further arranged for performing an analysis of the tissue type and/or condition, and providing a control unit (170) connected to the optical unit, the control unit being capable of generating a feedback control signal (FEEDCON) based on the analysis of the tissue type and/or condition.

* * * * *